United States Patent

Kuth et al.

[11] Patent Number: 5,944,663
[45] Date of Patent: Aug. 31, 1999

[54] APPARATUS FOR TREATMENT WITH ACOUSTIC WAVES

[75] Inventors: Rainer Kuth, Herzogenaurach; Siegfried Schneider, Erlangen; Ulrich Schätzle, Röttenbach, all of Germany

[73] Assignee: Siemens Aktiengesellschaft, Munich, Germany

[21] Appl. No.: 08/930,174

[22] PCT Filed: Apr. 17, 1996

[86] PCT No.: PCT/DE96/00672

§ 371 Date: Oct. 9, 1997

§ 102(e) Date: Oct. 9, 1997

[87] PCT Pub. No.: WO96/33666

PCT Pub. Date: Oct. 31, 1996

[30] Foreign Application Priority Data

Apr. 28, 1995 [DE] Germany ............... 195 15 748

[51] Int. Cl.⁶ ........................................ A61B 5/00
[52] U.S. Cl. .................. 600/411; 600/412; 600/426; 600/427; 600/439; 601/3; 601/4
[58] Field of Search .................. 600/427, 407, 600/410, 411, 412, 426, 439, 414; 606/130; 601/2, 3, 4

[56] References Cited

U.S. PATENT DOCUMENTS

| 4,617,931 | 10/1986 | Dory . | |
|---|---|---|---|
| 4,764,944 | 8/1988 | Finlayson . | |
| 5,081,984 | 1/1992 | Wess et al. . | |
| 5,107,839 | 4/1992 | Houdek et al. . | |
| 5,275,165 | 1/1994 | Ettinger et al. ................. | 128/653.2 |
| 5,389,101 | 2/1995 | Heilbrun et al. . | |
| 5,443,068 | 8/1995 | Cline et al. .................. | 128/653.5 |
| 5,590,653 | 1/1997 | Aida et al. .................. | 128/653.2 |
| 5,772,594 | 6/1998 | Barrick .................. | 600/407 |

FOREIGN PATENT DOCUMENTS

| 0 534 607 | 3/1993 | European Pat. Off. . |
|---|---|---|
| 0 614 651 | 9/1994 | European Pat. Off. . |
| OS 42 07 632 | 9/1993 | Germany . |
| OS 42 29 817 | 3/1994 | Germany . |
| 5-300910 | 11/1993 | Japan . |
| WO 91/04711 | 4/1991 | WIPO . |
| WO 95/07055 | 3/1995 | WIPO . |

*Primary Examiner*—Ruth S. Smith
*Attorney, Agent, or Firm*—Hill & Simpson

[57] ABSTRACT

In an apparatus for treatment of a subject with acoustic waves, a spatial allocation, required for the treatment of the patient and a source of acoustic waves relative to each other is effected by a surgical work station using a three-dimensional navigation system on the basis of a number of images of a region to be treated, which are obtained independently of the treatment apparatus, in different coordinate systems, and are displayed on a display screen of the work station.

52 Claims, 8 Drawing Sheets

APPARATUS FOR TREATMENT WITH ACOUSTIC WAVES

BACKGROUND OF THE INVENTION

1. Field of the Invention

The present invention is directed to an apparatus for treating a subject with acoustic waves, of the type having an acoustic wave source which produces acoustic waves that are focused onto a therapeutic effective region, means for displacing the therapeutic effective region and the subject relative to each other, means for displaying an image of a body region of the subject which is to be treated with the focused acoustic waves, and means for mixing a mark which indicates the position of the therapeutic effective region into the displayed image.

2. Description of the Prior Art

Apparatuses of this sort are known for example from European Application 0 148 653 and from the book Biliary Lithotripsy (eds. J. T. Ferrucci et al.), Adapted from the Proceedings of the First International Symposium on Biliary Lithotripsy, Jul. 11–13, 1988, pages 253–263, 263a; B. Forssmann et al.: "Dornier: MPL 9000 Multipurpose Lithotripter." In this apparatus, focused ultrasound waves are produced as acoustic waves. One or several ultrasound tomograms of the body region to be treated containing the focus of the ultrasound waves, obtained by means of an ultrasound location apparatus, are displayed. In the case of European Application 0 148 653, an ultrasound transducer is provided for this purpose, connected with the source in such a way that the imaged body region contains the therapeutic effective region of the ultrasound waves. In the case of the MPL 9000 Multipurpose Lithotripter, another adjustable ultrasound transducer is additionally provided, by means of which a second body slice containing the body region to be treated can be displayed.

In order to treat a particular body region, in the known apparatus the source, including the ultrasound transducer of the ultrasound location apparatus, is first displaced relative to the body of the subject to be treated until the body region to be treated is imaged in the ultrasound tomogram, and the mark coincides with the body region to be treated. The charging of the region to be treated with the focused ultrasound waves then takes place.

The known apparatus can be used only conditionally, in cases in which the body region to be treated differs sufficiently from the structures surrounding it with respect to its acoustic characteristics to enable a sufficiently clear representation in an ultrasound tomogram.

In order to provide aid here, in the case of an apparatus known from EP 0 534 607 A1 a magnetic resonance (MR) diagnostic apparatus is provided as a location apparatus. Though nothing is then left to be desired even during the treatment with respect to the image quality of the image information provided, particularly in the representation of tumors, it is however extremely expensive to use an MR diagnostic apparatus as a location apparatus, since this apparatus is not available for other purposes while a treatment is being carried out. Moreover, the patient is accessible by the medical personnel only with difficulty, due to the presence of magnets and radio-frequency coils.

SUMMARY OF THE INVENTION

An object of the invention is to provide an apparatus of the general type above initially described which allows a reliable location and treatment of a body region in a simple and cost-effective way even of those body regions that cannot be imaged in ultrasound images, or that can be so imaged only with insufficient clarity, without requiring a diagnostic apparatus necessary for location during the entire duration of the treatment, and in such a way that the treatment can nonetheless ensue using image information obtained during the location.

The above object is achieved in accordance with the principles of the present invention in an apparatus for treating a subject with acoustic waves of the type initially described above, which additionally includes means for acquiring the spatial position of the therapeutic effective region and the orientation of the acoustic wave source relative to a first spatial coordinate system, means for acquiring the spatial position and the orientation of the subject relative to a second spatial coordinate system, means for displaying an image wherein the spatial position and the orientation of the body region to be treated can be determined relative to a third spatial coordinate system, and means for mixing a mark into the displayed region, indicating the position of the therapeutic effective region, using data identifying the spatial position of the therapeutic effective region and the orientation of the source relative to the first spatial coordinate system, data identifying the spatial position and the orientation of the subject to be treated relative to the second spatial coordinate system, data identifying the spatial position and orientation of the body region to be treated relative to the third spatial coordinate system, and data identifying the respective spatial positions of the first, second and third spatial coordinate systems relative to one another.

It is thus possible to produce an image of the body region to be treated before the treatment and independent of the apparatus for the treatment, with an imaging diagnostic apparatus (e.g., a magnetic resonance tomograph, a computer tomograph or an X-ray diagnostic apparatus) optimally matched to the characteristics of the respective body region to be treated, and to carry the treatment out at a later time with the displaying of the image by the display means. The respective diagnostic apparatus is thus required only during the time necessary for the production of the image, and not during the entire duration of the treatment. Since the mixing of the mark indicating the position of the therapeutic effective region into the image of the diagnostic apparatus, taking into account the spatial position of the therapeutic effective region and the orientation of the source, the spatial position and orientation of the subject to be treated and the spatial position and orientation of the body region to be treated, takes place during the production of the image, a reliable location and treatment of the body region to be treated is possible despite the fact that the therapy apparatus itself contains no location apparatus in the sense of an imaging diagnostic apparatus, or need contain no such apparatus.

In the simplest case, the displacement means can contain a hand-held freely displaceable source. While observing the image displayed by the display means, the treating physician then directs the source in such a way that the mark in the image indicating the position of the therapeutic effective region is respectively located at the point that is to be charged with the acoustic waves, and then activates the source for the emission of the acoustic waves.

The displacement means can however also contain a motorized adjustment unit for the source, whereby operating elements are preferably allocated for the manual operation of the adjustment unit. The source is then oriented via the motorized adjustment unit, manually controlled in a corresponding manner by the operating elements, in such a way that the mark indicating the position of the therapeutic effective region coincides with the respective body region to be treated, before the source for the emission of the acoustic waves is activated.

In order to further reduce the risk of faulty treatments, according to a preferred embodiment of the invention means are provided for marking the respective body region to be treated, by means of which a marking identifying the body region to be treated, preferably surrounding it, can be mixed into the image displayed by the display means. Before the beginning of the actual treatment, a region can then be marked within which the focus zone is to be displaced during the treatment. The marking thus serves as a guideline, so to speak, for the treating physician, i.e., he will activate the source for the emission of acoustic waves only if the mark indicating the position of the therapeutic effective region is located within the marking. According to a particularly preferred embodiment of the invention, it is provided that the source can be activated for the production of acoustic waves only when the therapeutic effective region is located inside the body region to be treated, corresponding to the marking. This can easily ensure the controlling of the therapy apparatus by permitting an activation of the source only if the mark indicating the position of the therapeutic effective region lies inside the marking.

The above object is also achieved in a further embodiment of an apparatus for treatment with acoustic waves in accordance with the invention, which also includes the initially described components, and in addition includes means for acquiring the spatial position of the therapeutic effective region and the orientation of the source relative to a first spatial coordinate system, means for acquiring the spatial position and the orientation of the subject to be treated relative to a second spatial coordinate system, means for displaying an image which allows the spatial position and the orientation of the body region to be treated to be determined relative to a third spatial coordinate system, means for marking the body region to be treated which allows a mark to be mixed into the displayed image, and a control unit which actuates the displacement means for causing the therapeutic effective region to come to lie in the body region to be treated which is identified by the marking, the control unit being supplied with and using for this purpose data identifying the spatial position of the therapeutic effective region and the orientation of the source relative to the first spatial coordinate system, data identifying the spatial position and the orientation of the subject to be treated relative to the second spatial coordinate system, data identifying the spatial position and orientation of the body region to be treated relative to the third spatial coordinate system, data identifying the respective spatial positions of the first, second and third coordinate systems relative to one another, and data identifying the position of the marking in the displayed image.

In contrast to the first embodiment during the production of the image the data concerning the spatial position of the therapeutic effective region and the orientation of the source, the spatial position and the orientation of the subject to be treated and the spatial position and orientation of the body region to be treated are thus used not for mixing in a mark indicating the position of the therapeutic effective region, but rather to enable a control unit to actuate the displacement means in such a way that the therapeutic effective region lies in the body region identified by means of a marking that can be mixed in using marking means. In the case of the second embodiment as well, a reliable location and treatment of the respectively relevant body region is thus possible, although the image forming the basis for the location and treatment was produced before the treatment, and was produced using an imaging diagnostic apparatus that is independent of the therapy apparatus.

In order to enable the treating physician to monitor the therapy process, according to a particularly preferred variant of the invention means for mixing in are provided that mix a mark indicating the position of the therapeutic effective region into the image.

The image displayed by the display means can be an image containing the image information of at least one tomogram. However, a perspectival image can also be displayed, calculated e.g. from several tomograms, from the data produced by means of a computer tomograph in spiral scan mode, or from the data obtained by means of an MR diagnostic apparatus, or from the images obtained by means of a conventional X-ray diagnostic apparatus, given defined different directions of transillumination. The perspective image can be shown partly in section.

In some circumstances, it can be useful for the display means to display several images at the same time, in order to provide the physician this way with comprehensive information. For this purpose, in a version of the invention the mixing-in means mix a mark indicating the position of the therapeutic effective region into several images, and/or a marking indicating the body region to be treated can be mixed into several images by the marking means.

According to a particularly preferred embodiment of the invention, the means for acquiring the spatial position of the therapeutic effective region and the orientation of the source and/or the means for acquiring the spatial position and the orientation of the subject to be treated contain a commercially available 3D navigation system. A navigation system of this sort is preferably also used to acquire the spatial position and orientation of the region to be treated in the production of the image.

According to a further preferred variant of the invention, the display means contain a commercially available surgical work station, which can at the same time also fulfill the function of the means for mixing in and the marking means.

In the interest of a reduced computing expense, it can be useful if at least the first and second coordinate system are identical.

Under certain circumstances, it can be useful if the therapy apparatus does nonetheless contain image production means. Such image production means, however do not serve for the production of an image used for location purposes, but are instead used to produce a temperature difference which is visible in an image obtained using the image production means, by means of brief activation of the source and/or activation of the source with reduced intensity. This enables corrections to be made in the event that the position of the temperature difference identified in the displayed image deviates from the position which the therapeutic effective region should have, according to the relevant data.

In some circumstances, it can be useful in this context to use the image production means to produce a further image before the activation of the source, in order to enable the determination of the position of the temperature change brought about by the activation of the source by means of comparison of the two images. The comparison of the two images thereby usefully ensues by means of subtraction. The image production means can be formed by means of an ultrasound diagnostic apparatus. It is also possible to use a magnetic resonance diagnostic apparatus as the image production means, operated with temperature-sensitive measurement sequences.

In a further variant of the invention, an image corresponding to the image displayed by the display means is produced after treatment is at least partially executed, or is completed, and those regions in which tissue changes were caused by the acoustic waves are determined by comparing the two images, and the display means display, in an image, the position and shape of those regions in which tissue changes were caused by the acoustic waves. Here as well, the comparison of the two images can ensue by means of subtraction.

In the following, the invention is specified on the basis of the attached figures, with reference to the example of the treatment of a tumor.

DESCRIPTION OF THE PREFERRED EMBODIMENTS

Figure 1:
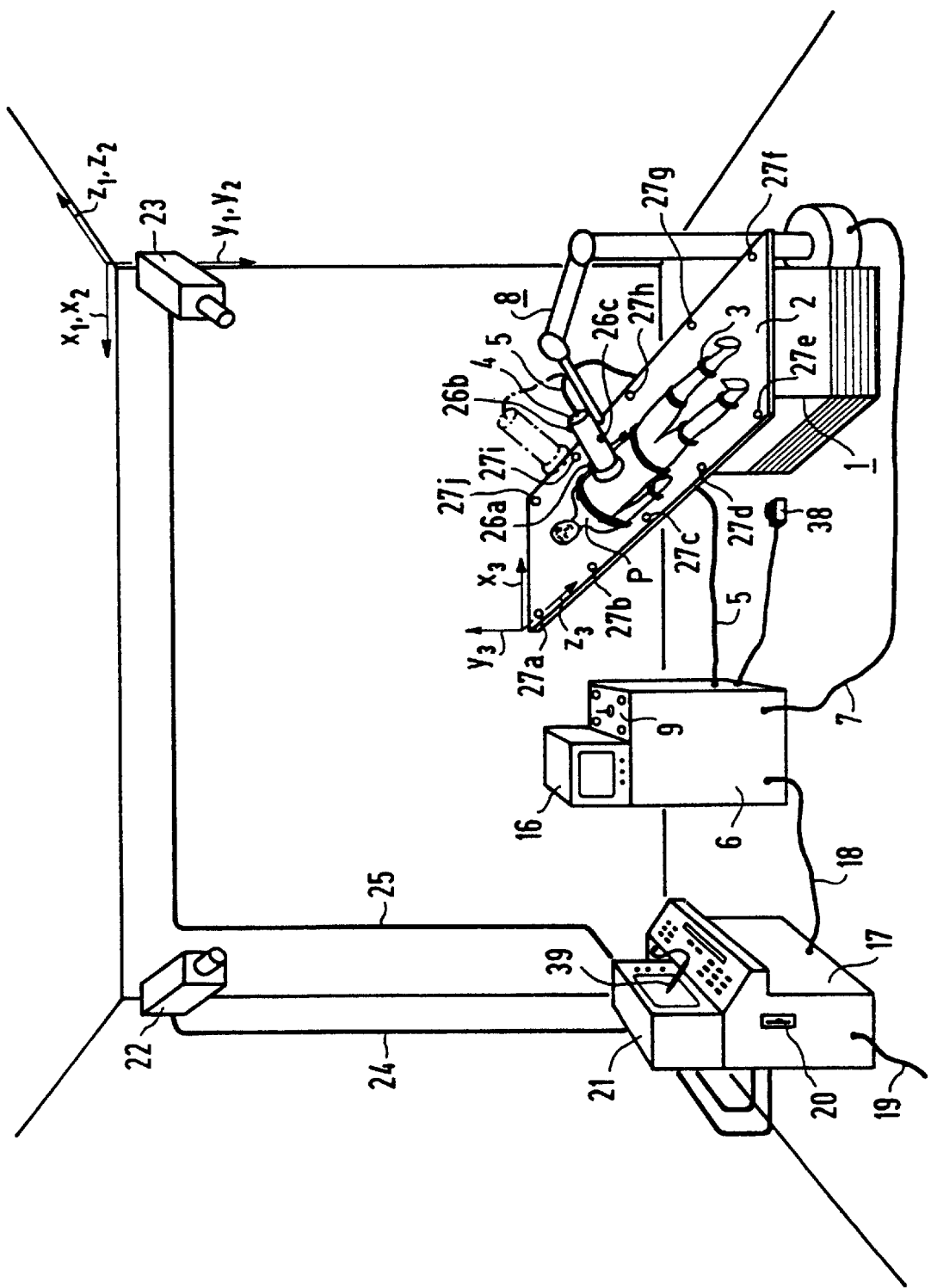
FIG. 1 illustrates the basic components of a therapy apparatus constructed in accordance with the principles of the present invention, contained in a treatment room.

As shown in FIG. 1, the inventive therapy apparatus includes a treatment table designated as a whole with 1, on whose positioning slab 2 a patient P is fixed in supine position by means of several belts, of which one is designated with 3.

For the treatment of the patient with acoustic waves, a therapy head 4 is provided, which contains a source of acoustic waves that radiates focused ultrasound waves. The therapy head 4 is connected to a supply unit 6 via a cable 5. A motorized adjustment unit 8 for the therapy head 4 attached to this unit, said adjustment unit being fashioned in the manner of a robot arm, is connected to this supply unit via a further cable designated 7.

The control and supply unit 6 includes an operating console 9 with the operating elements required for the operation of the therapy head 4 and the adjustment unit 8.

Figure 3:
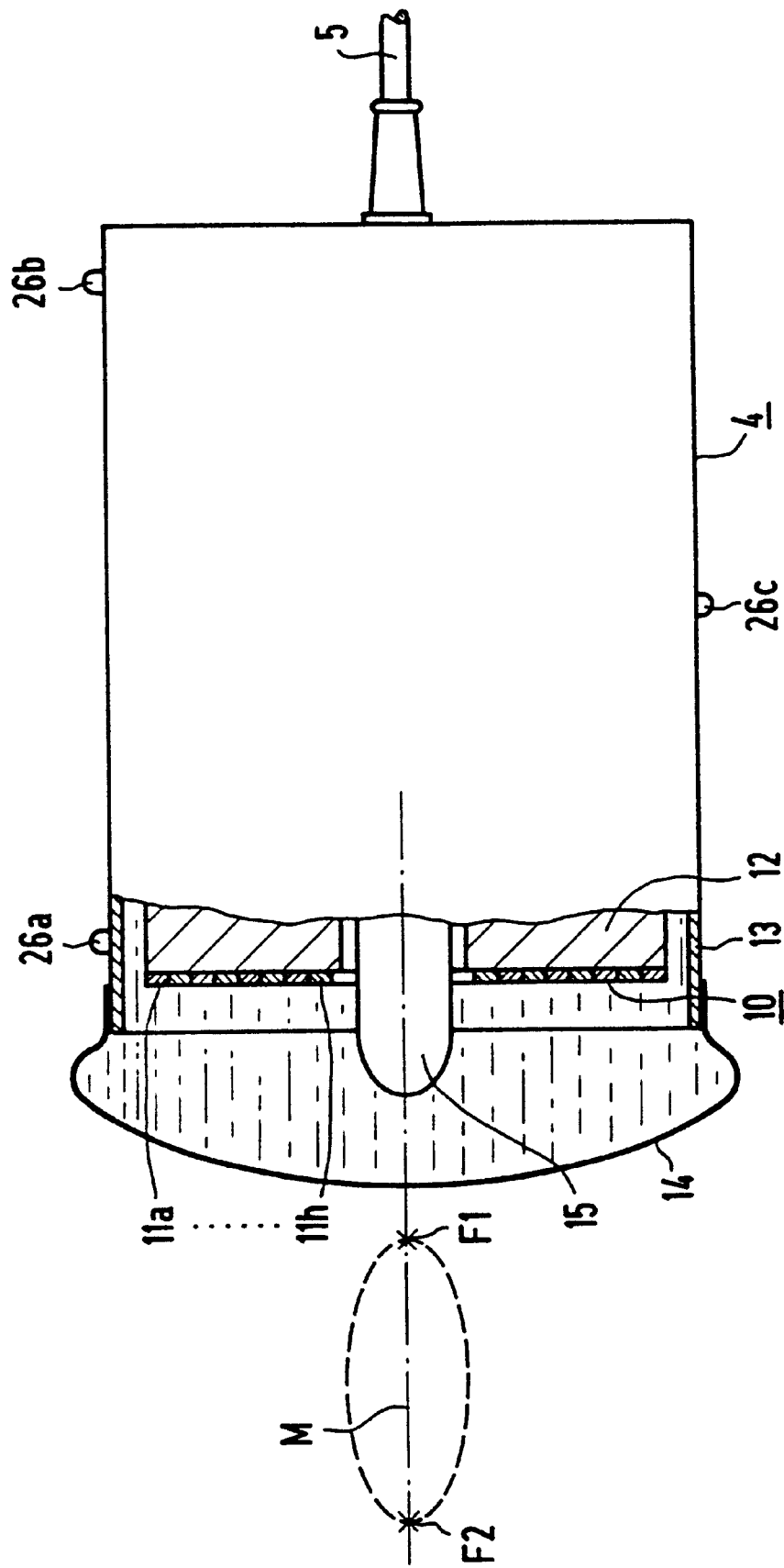
FIG. 3 is a side view, partly in section, of an acoustic wave source for use in the apparatus of FIG. 1.

In the case of the specified exemplary embodiment, the therapy head 4 shown in FIG. 3 contains a piezoelectric therapeutic ultrasound source 10, constructed in the manner of a phased array, whose ultrasound transducer elements are attached in mosaic fashion on a suitable bearer element 12 (backing). In FIG. 3, some of the ultrasound transducer elements are visible and are designated $11a$ to $11h$. In addition, a higher degree of effectiveness of the ultrasound source is achieved if this source is an "air backed" source i.e., no supporting element, and the backsides of the ultrasound transducer elements accordingly border on air. This can be achieved by means of a self-supporting construction of the ultrasound source, or by using, if present, a matching layer provided for impedance matching between the ultrasound source and the acoustic propagation medium as a supporting element for the ultrasound transducer elements.

The source 10 is housed in a housing 13 that is sealed at its application end by means of a flexible coupling membrane 14 and is filled with a suitable liquid acoustic medium of propagation, e.g. water.

As a result of the construction of the source 10 as a phased array, it is possible, by means of suitable controlling of the ultrasound transducer elements, to displace the focus zone of the therapeutic ultrasound waves electronically, in a known manner, relative to the source 10, within a spatial region that is indicated with broken lines in FIG. 3. In FIG. 3, as an example, for the position of the focus zone located furthest from the source 10 and the position located closest to the source 10, the respective centers of focus zones are identified with a cross and designated with $F_2$ and $F_1$.

The desired position of the focus zone relative to the source 10 can be set with the operating elements provided on the control and supply unit 6; the control and supply unit 6 then drives the ultrasound transducer elements $11a$ to $11h$ of the source 10 in phase-shifted fashion in the manner required.

In a central opening of the source 10, there is arranged a diagnostic ultrasound applicator 15, for purposes to be explained below, which works together with electronics contained in the control and supply unit for the production of an ultrasound image of a sector-pattern layer, indicated with broken lines in FIG. 3, which can be displayed as needed on a screen 16 allocated to the control and supply unit 6.

Moreover, the inventive therapy apparatus includes a commercially available surgical workstation 17 (e.g. "The Viewing Wand ®" by ISG Technologies, Toronto, Ontario, Canada), which is connected with the control and supply unit 6 via a cable 18.

Image data, which are displayed on a screen 21 of the work station 17, can be supplied to the work station 17 via a further cable 19 or a diskette inserted into a disk drive 20 of the work station 17. The standard image manipulations can be carried out by means of the work station 17.

In relation to a commercially available work station, the work station 17 is expanded by two video cameras 22 and 23, which are connected to the work station 17, attached in two corners of the treatment chamber in the corner region, via corresponding cables 24 and 25.

In connection with three laser diodes $26a$ to $26c$ fixedly attached at defined points on the housing of the therapy head 4, the video cameras 22, 23 serve on the one hand to determine the spatial position and orientation of the therapy head 4, and thereby of the source 10, as well as the spatial orientation of the midaxis M of the source 10 in relation to a first spatial coordinate system $x_1$, $y_1$, $z_1$, shown in FIG. 1. This takes place in that the work station 17 evaluates the images of the video cameras 22 and 23 with respect to the coordinates of the images of the laser diodes $26a$ to $26c$, and from these coordinates calculates the spatial position and the orientation of the therapy head 4 or of the source 10, as well as the orientation of the midaxis of the source 10 with respect to the first coordinate system. Since data concerning the set position of the focus zone are additionally supplied to the work station 17 via the line 18, the work station 17 is moreover able to determine the spatial position of the focus zone in the first coordinate system.

The video cameras 22 and 23, in combination with laser diodes $27a$ to $27j$ attached fixedly along the longitudinal sides, at defined locations on the positioning slab 2, serve to generate signals for determining the spatial position and orientation of the patient P relative to a second spatial coordinate system $x_2$, $y_2$, $z_2$, which is identical with the first coordinate system. This determination takes place by means of an evaluation in the work station 17 of the images of the video cameras with respect to the images of the laser diodes 27a to 27j, and a calculation by the work station 17 of the spatial position and orientation of the positioning slab 2 from these coordinates. Since the patient P is fixed (immobilized) on the positioning slab 2, the spatial position and orientation of the patient P is known.

In order to be able to use an image displayed on the screen of the work station 17 of a body region to be treated of the patient P in the same way as the image of the location means of a conventional therapy apparatus for the positioning of the focus zone of the ultrasound waves in the region to be treated, it is necessary to be able to determine the spatial position and orientation of the patient P, and thereby of the region to be treated, relative to the first or second spatial coordinate system. Corresponding data must thus be obtained during the production of the image.

Figure 2:
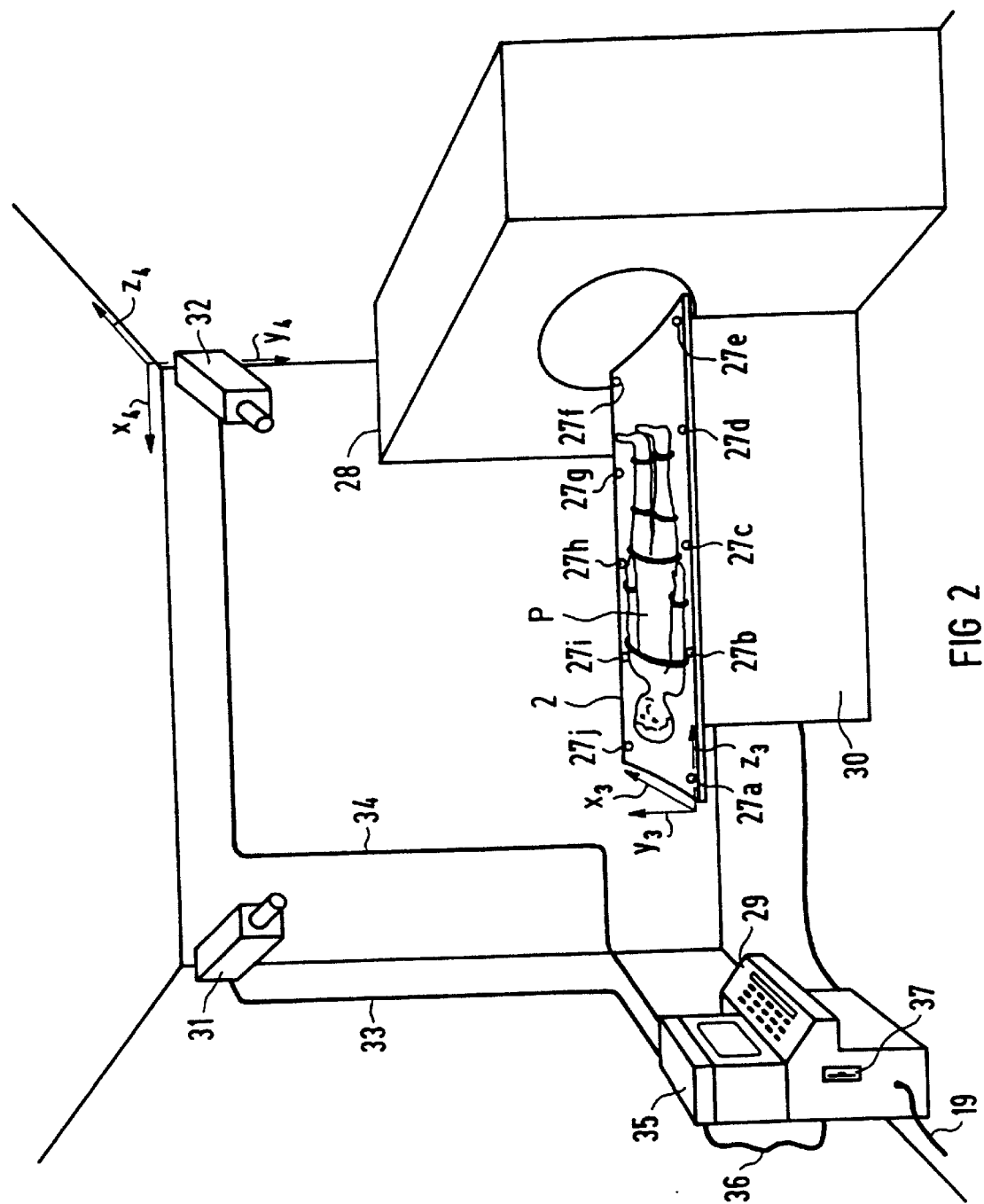
FIG. 2 shows the basic components for the production of an image of the body region to be treated, this image being required for the operation of the therapy apparatus of FIG. 1.

The way in which this takes place can be seen in FIG. 2, which shows as an example an MR diagnostic apparatus 28 with an associated operating and display unit 29, which serves to obtain an image (a tomogram) of the body region to be treated of the patient 8.

The procedure which is followed is that the patient P, fixed on the positioning slab 2 by means of the belts in a bodily posture and position suitable for the treatment (the position during the exposure is maintained unaltered during the treatment), is set on the patient positioning means 30 of the MR diagnostic apparatus 28 together with the positioning slab 2.

Video cameras 31 and 32 are also attached in the chamber in which the MR diagnostic apparatus 28 is located, which are connected with an image processing unit 35 via cables 33 and 34.

The video cameras 31 and 32 and the image processing unit 35 serve to determine the position of the sectional plane of the tomogram of the body region to be treated of the patient P, produced by means of the MR diagnostic apparatus, and thereby of the body region to be treated itself, in a third spatial coordinate system $X_3$, $y_3$, $Z_3$. The third coordinate system is related to the positioning slab 2, whereby the respective axes $X_3$ and $Z_3$ of the transverse and longitudinal sides of the positioning slab 2 correspond, and the axis $y_3$ stands at a right angle to the $x_3$ and $z_3$ axes.

The position of the sectional plane respectively set at the MR diagnostic apparatus 28 in a fourth spatial coordinate system, e.g. in the coordinate system $X_4$, $y_4$, $Z_4$, with coordinate origin in the upper right corner of the chamber, is known. The position of the third coordinate system, and thereby the position of the patient P in the fourth coordinate system, can be determined from the coordinates in the fourth coordinate system of the laser diodes 27a to 27j, attached to the positioning slab 2. The image processing unit 35 produces data corresponding to the coordinates of the laser diodes 27a to 27j to the operating and display unit 29 of the MR diagnostic apparatus 28 via a cable 36. This unit 35 adds the data concerning the position of the sectional plane and of the laser diodes 27a to 27j in the fourth coordinate system to the image data corresponding to the produced image of the body region to be treated. The aforementioned data can then be transmitted to the control and supply unit 6 of the inventive therapy apparatus via a cable 18. It is also possible, however, to write the aforementioned data onto a diskette by means of a diskette drive 37 of the operating and display unit 29, and to insert this diskette into the diskette drive 20 of the work station 17.

The work station 17 now calculates the position of the sectional plane of the image in the third coordinate system. Since, moreover, the position of the focus zone in the first coordinate system, the position of the patient in the second coordinate system, and, in addition, the positions of the first, second and third coordinate system relative to one another are known, the work station 17 is now able to mix a mark corresponding to the position of the focus zone into the image produced by means of the MR diagnostic apparatus 28 and displayed on the screen 21. This is illustrated in FIG. 4, which shows a tomogram of an internal organ that has a tumor T, namely the liver L, of a patient, which image was produced using the MR diagnostic apparatus and is now displayed on the display screen 21 of the work station 17.

Figure 4:
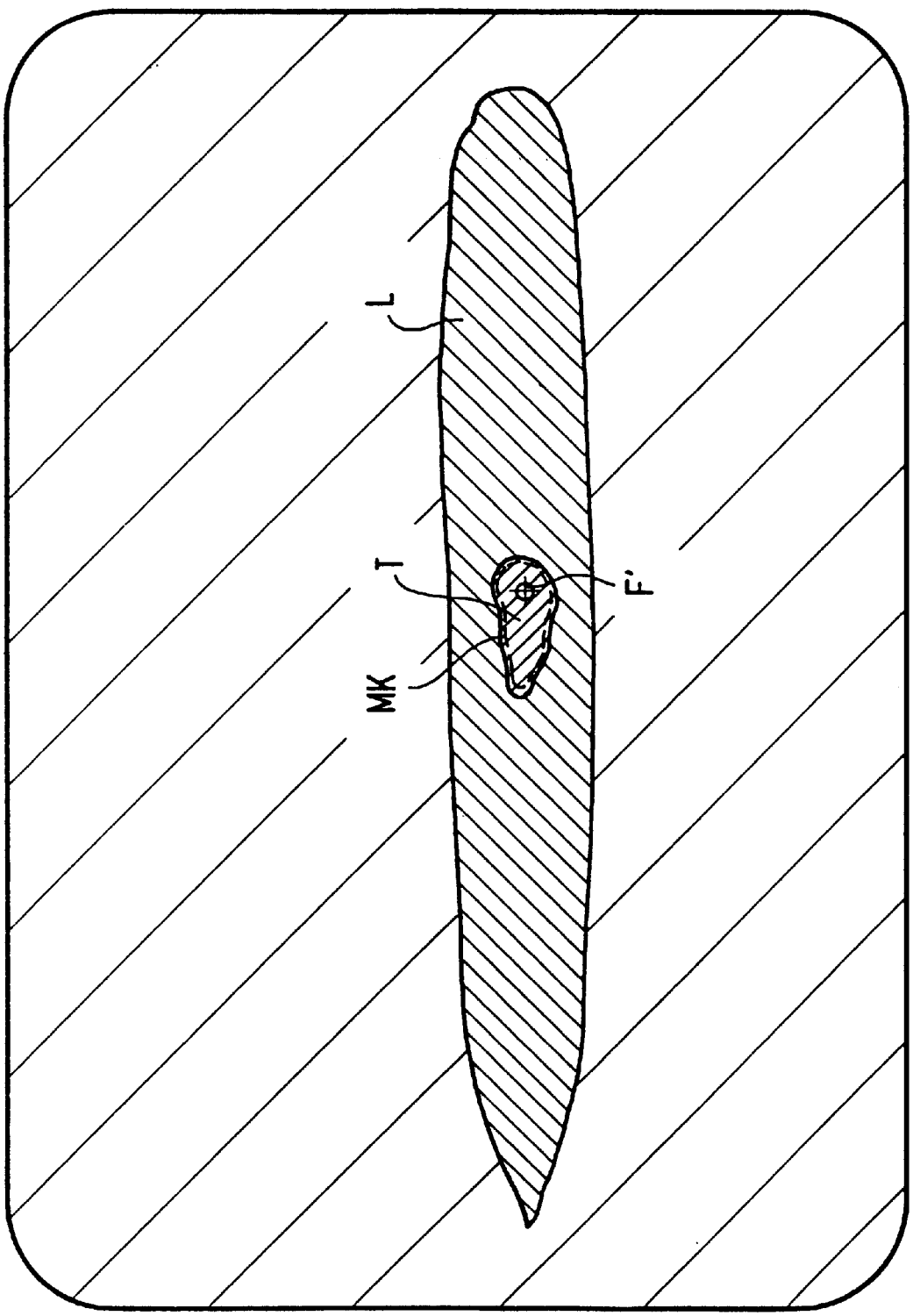
FIGS. 4–8 respectively show various images which can be displayed on the display screen of the therapy apparatus of FIG. 1, for explaining the operation of that therapy apparatus.

In the treatment situation shown in FIG. 4, the center of the focus zone of the ultrasound waves is inside the tumor T, which is shown by the position of the mark F', representing the center of the focus zone of the ultrasound waves. The treatment with focused ultrasound waves is thus possible without danger.

For the treatment of the tumor T with focused ultrasound, according to a first type of operation of the inventive therapy apparatus the treating physician uses the operating elements provided on the operating console 9 of the control and supply unit 6 to bring the therapy head 4 into a position, by means of the adjustment unit 8, such that the coupling membrane 14 lies snugly on the bodily surface of the patient P. Subsequently, the treating physician uses the operating elements provided on the operating console 9 to actuate the adjustment unit 8 in such a way that the mark F' is located inside the tumor T in the tomogram shown on the display screen 21 of the work station 17. The treating physician now actuates a foot switch 38 connected to the control and supply unit 6, whereby the source 10 is made to emit an ultrasound pulse whose energy content is sufficient to heat the tumor tissue located in the focus zone, according to the type of treatment, to a temperature between 42 and 45° C. (called hyperthermia, by means of which the metabolism of the tumor cells is intended to be disturbed) or to a temperature above 45° C., (called thermotherapy, by means of which the tumor tissue is intended to be necrotized). Subsequently, the physician electronically displaces the focus zone slightly, by means of corresponding actuation of the operating elements of the operating console 9 while observing the mark F', and reactuates the foot switch 38. This is repeated until the entire region of the tumor T shown in the tomogram is treated. If the electronic range of displacement of the focus zone is not sufficient to treat the entire region of the tumor shown in the tomogram, it is additionally necessary to displace the therapy head 4 relative to the body of the patient P in the way required, using the adjustment unit 8.

In order to avoid unintentional treatment of healthy tissue, it is possible to bypass a region to be treated in the tomogram shown on the display screen 21 by means of a light pen 39 shown in FIG. 1, whereupon a marking MK (see FIG. 4) is mixed into the tomogram, which marking serves as an aid to orientation.

In addition, in order to preclude faulty treatments, in a variant of the first-described type of operation, when the foot switch 38 is actuated the control and supply unit 6 activates the source 10 for the emission of ultrasound waves only if the mark F' is located inside the marking MK. For this purpose, the work station 17 gives a signal to the control and supply unit 6, which indicates to the latter whether the mark F' lies inside or outside the marking MK.

The described variant is particularly important when, in a modification of the first-described type of operation, the treating physician separates the therapy head from the adjustment unit 8 in the way shown in broken lines in FIG. 1, in order to orient it in hand-held fashion while observing the tomogram shown on the screen 21, in such a way that the mark F', and therewith the focus zone of the ultrasound, is located at the location respectively to be treated.

According to a second type of operation, the displacement of the focus zone of the ultrasound, and, if required, of the therapy head 4, ensues automatically, in such a way that the region of the tumor T located inside a marking MK set by means of the light pen 39 is treated, in step-by-step fashion if necessary. It is optionally possible to mix the marking F', indicating the position of the focus zone, into the tomogram as well, in addition to the marking MK, as is also shown in FIG. 4. The data required for the automatic control are supplied to the control and supply unit 6 by the work station 17.

Figure 5:
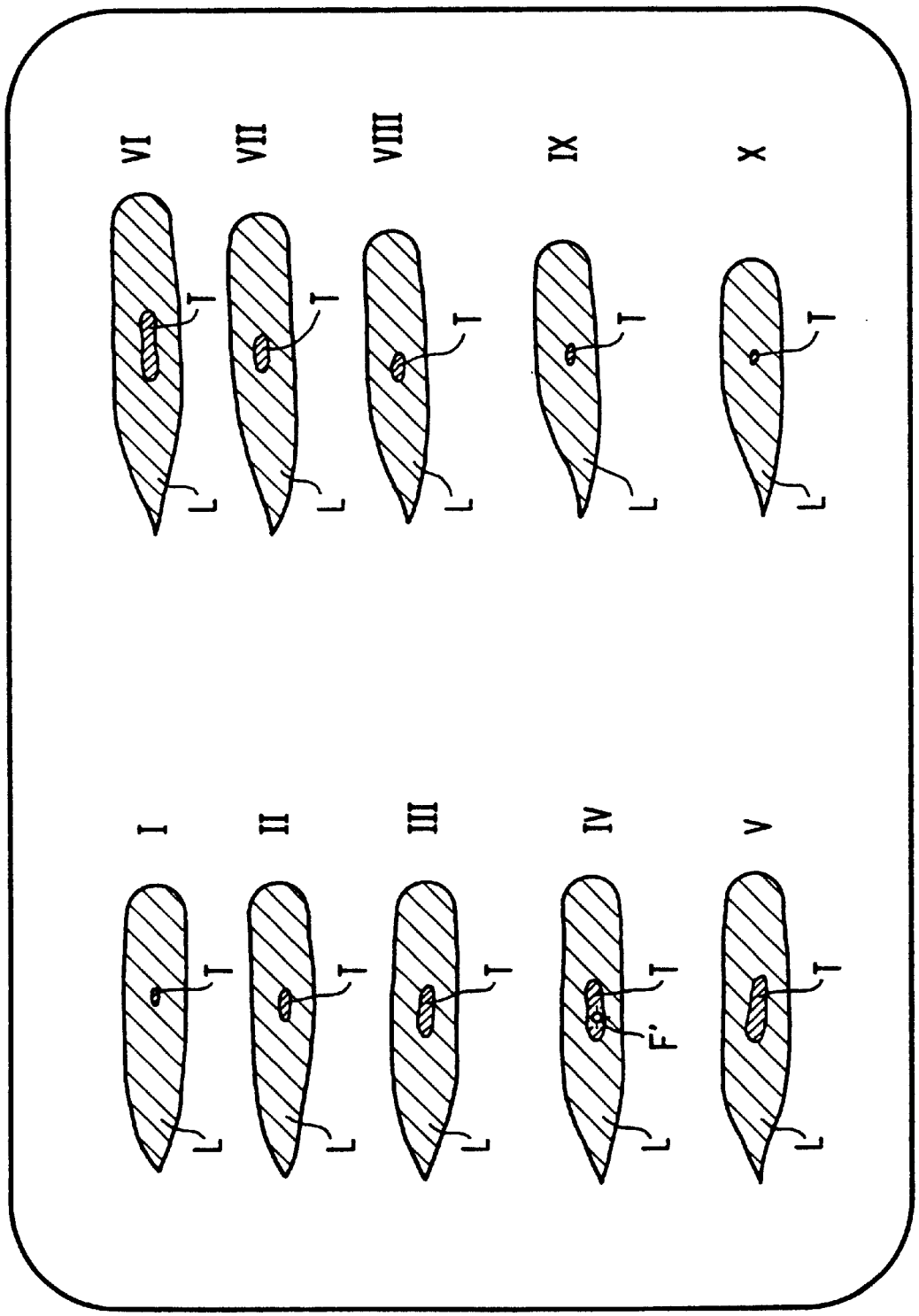

Since generally the body region respectively to be treated is not located in its entirety in a single body slice that can be represented by means of the MR diagnostic apparatus 28, before the treatment it is useful to produce images of several body slices that are adjacent to one another and that contain the body region to be treated, and to determine the position of the sectional plane in relation to these images. These images are then shown simultaneously on the screen 21 of the work station 17, as is the case in FIG. 5 for ten tomograms designated I to X. It is then possible to attach a marking MK in the individual tomograms using the light pen 39, analogously to the procedure specified above, in a way not shown in FIG. 5 for reasons of clarity, and then to treat the body region located inside the markings MK with focused ultrasound, manually in gradual fashion according to the first type of operation, or automatically according to the second type of operation. The mark F' identifying the position of the focus zone of the ultrasound is of course mixed only into the image of that body slice in which therapy is taking place at that moment. In the case of FIG. 5, this is the body slice shown in image IV.

Figure 6:
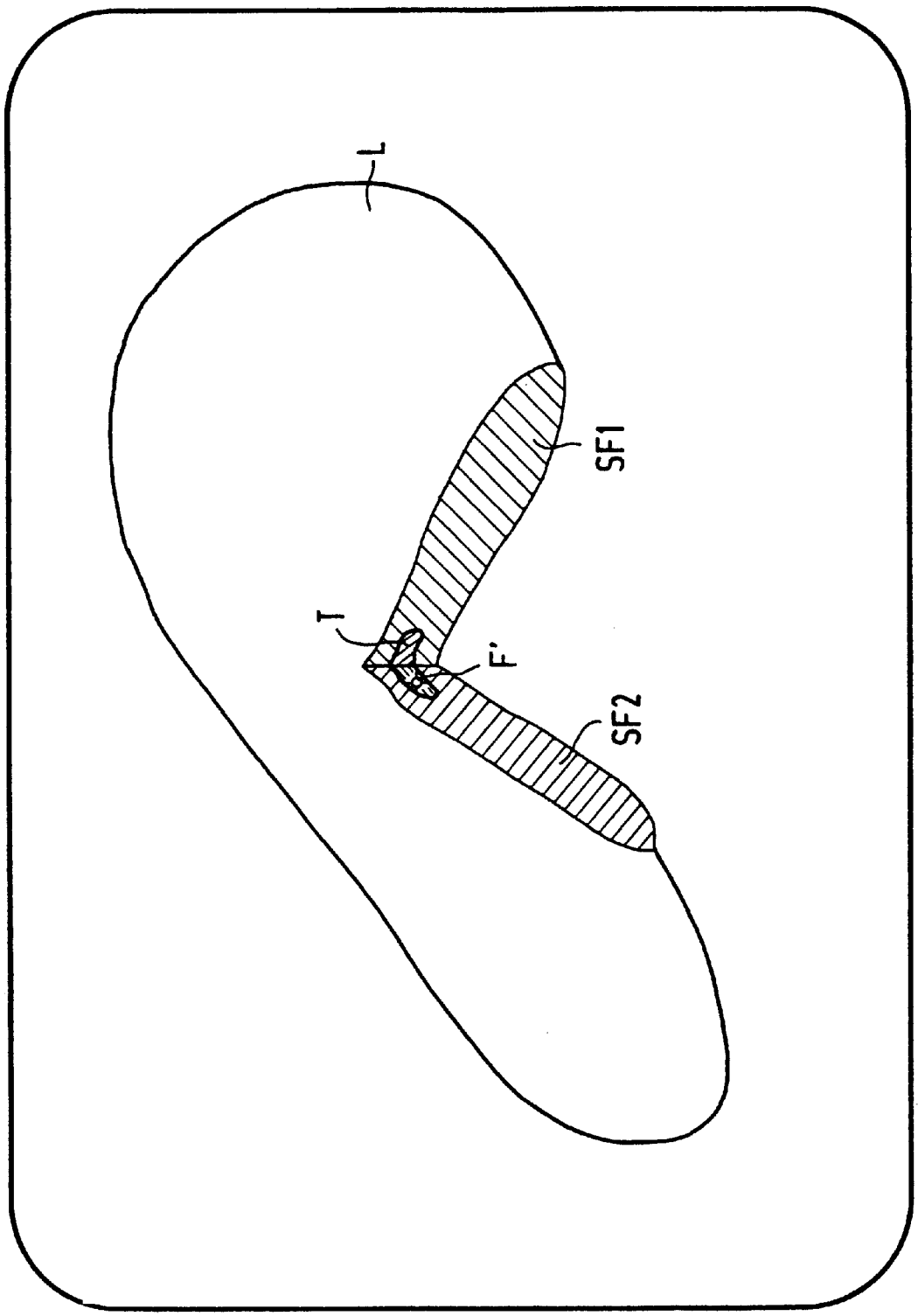

If images of several body slices adjacent to one another are produced in the way described above, the surgical workstation 17 is able to calculate a spatial image of the body region of interest, and to display it in perspective fashion. It is thereby possible to represent in perspective view an organ or a tumor located therein. It is particularly instructive for the treating physician if the perspectival image is shown partly sectionally, as is illustrated in FIG. 6, since spatial information concerning the liver L and the tumor T can then be learned from the image. In the case of FIG. 6, there are two slice surfaces meeting one another, $SF_1$ and $SF_2$, in the region of the tumor T.

Perspective images can do more than give the physician a good overview of the anatomical situation. They can also be used to position the focus zone of the ultrasound in the required way, which is illustrated in FIG. 6 in that the mark F' indicating the position of the focus zone is plotted in the region of the region of the tumor T lying in the slice surface $SF_2$.

As is known, differences between the theoretical and the actual position of the focus zone of the ultrasound can result due to refractions at tissue boundary layers. There is thus a danger that healthy tissue may be affected unintentionally.

In order to prevent this, in the case of the inventive apparatus a correction function can be activated both in the first and in the second type of operation. This is based on the fact that before an ultrasound pulse serving for the treatment is emitted, an ultrasound pulse with, optionally, an intensity so far reduced or a duration so far reduced that tissue damage is not to be expected is radiated emitted. A heating nonetheless then occurs in the region of the focus zone. This is detected by means of the ultrasound diagnostic apparatus according to a method specified in German OS 42 29 817, by producing a first ultrasound image before the emission of the ultrasound pulse with reduced intensity or duration, producing a second after the emission of the first, and comparing the two ultrasound images with one another by means of subtraction.

Figure 7:
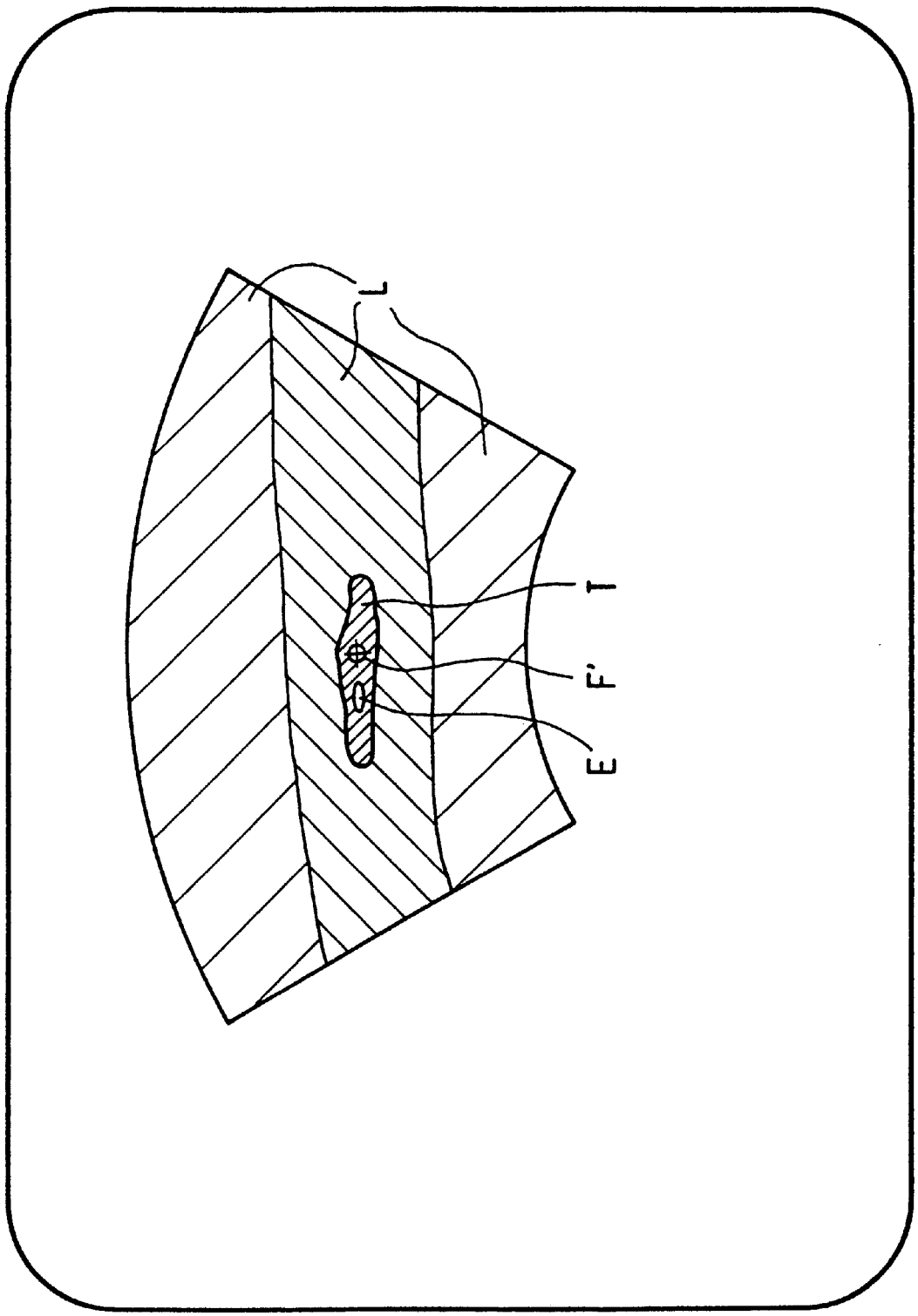

In the case of the inventive apparatus, this takes place by supplying the ultrasound images, produced before and after the ultrasound pulse with reduced intensity or duration, to the work station 17, which subtracts the two ultrasound images from one another, superposes the resulting image on the image produced after the emission of the ultrasound pulse with reduced intensity, and mixes the marking F' indicating the position of the focus zone into the image obtained in this way, and displays this image on the display screen 21 (see FIG. 7).

The treating physician can thus recognize without difficulty whether there are significant deviations between the theoretical position of the focus zone, identified by the mark F', and the actual position of the focus zone, corresponding to the position of the heating E, and can carry out corresponding corrections.

Automatic correction is also possible. In this case, the work station 17 determines the deviation existing between the theoretical and the actual focus position, using image processing methods known in themselves, and gives a corresponding signal to the control and supply unit, which corrects the driving of the ultrasound transducer elements of the source 10 before emitting the ultrasound pulse serving for treatment, in such a way that the actual position of the focus zone agrees with the position indicated by the mark F'.

In order to be able to check at which locations tissue modifications were effected by the ultrasound treatment, after completion of a part of the treatment or of the entire treatment, it is possible, given a patient 2 who is immobilized continuously on the positioning slab 2, to use the MR diagnostic apparatus 28 to again produce tomograms of exactly the same body slices in relation to which tomograms were produced before treatment.

The corresponding data are additionally supplied to the work station 17 via the cable 19 or via diskette, which station then compares with one another, preferably by means of subtraction, images corresponding to one another exposed before and after the treatment. On the basis of the subtraction images obtained in this way, the work station 17 then displays on its screen 21 those regions in which tissue modifications were caused by the focused ultrasound.

This is possible with particular clarity if the work station 17 calculates a partly sectional perspectival image on the basis of the images exposed before and after the treatment, from which those regions in which the focused ultrasound has caused tissue modifications are visible.

Figure 8:
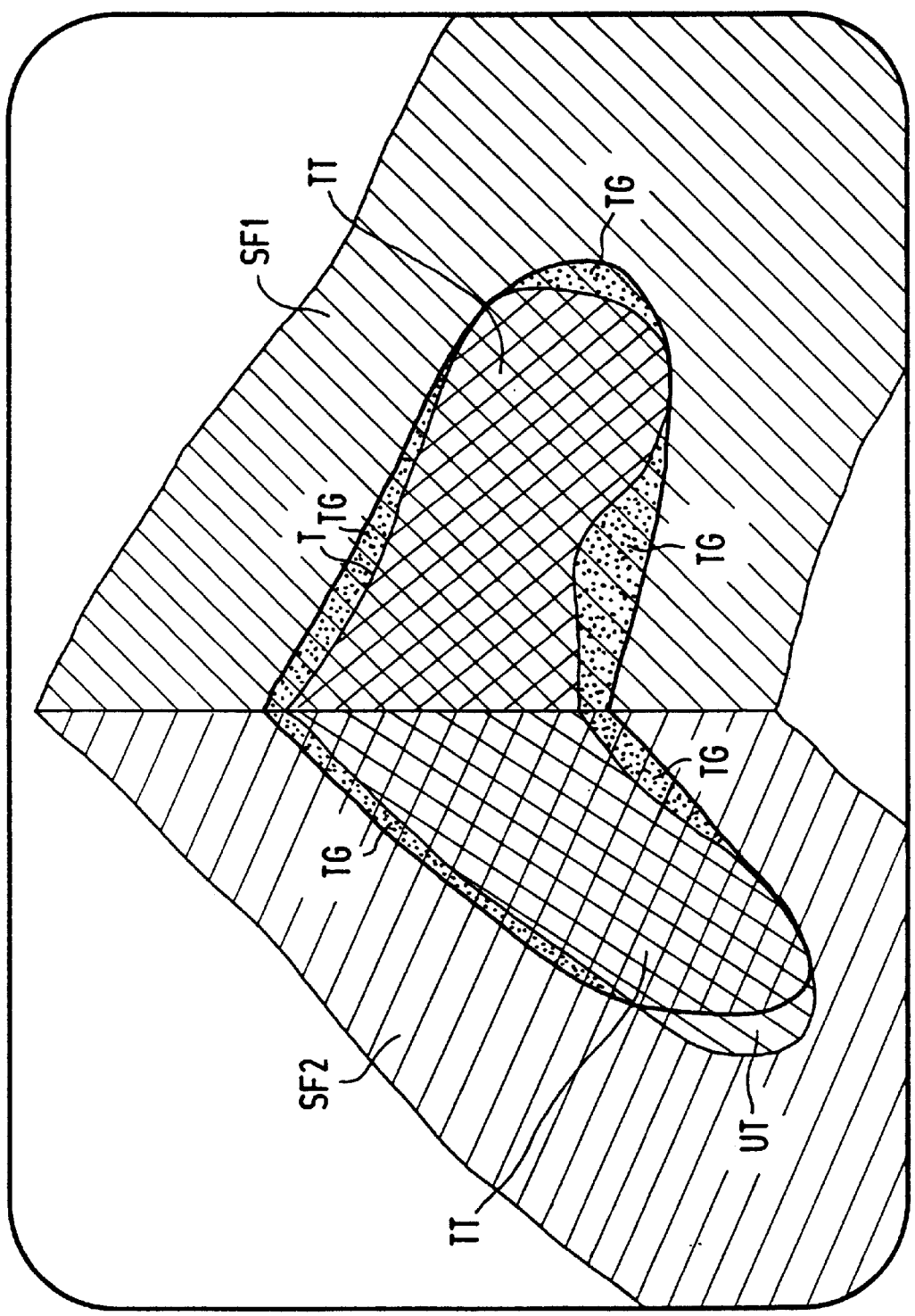

An image of this sort is shown in FIG. 8. This image is an enlargement of a segment of the image according to FIG. 6, in which, in the way described above, those regions in which tissue modifications were caused are emphasized. Those regions of the tumor in which tissue modifications were caused by the focused ultrasound are provided with crosshatching and are designated TT. Angled hatching and dots designate regions of "healthy" tissue in which tissue modifications were caused by the focused ultrasound. In addition, these regions are designated TG. A region of the tumor T in which no tissue changes were caused is identified with hatching that rises from left to right. This region is designated UT. The other regions are untreated healthy tissue.

The video cameras 22 and 23, and the laser diodes 26a to 26c as well as 27a to 27j on the one hand and the video cameras 31 and 32, the image processing unit 35 and the laser diodes 27a to 27j on the other hand are components of commercially available three-dimensional (3D) navigation systems, such as those available under the designation "Flashpoint®" from Pixsys Inc., Boulder, Colo., USA.

If, moreover, the immobilization described in the case of the specified exemplary embodiment cannot be expected of the patient, it is possible, in a way not shown, to attach a suitable stereotactic frame to the patient P, with laser diodes 27a to 27j attached thereto, in order to be able to determine the spatial orientation of the patient P.

Other 3D navigation systems, e.g. using already-mentioned stereotactic apparatuses, can be used in place of the systems provided in the specified exemplary embodiment.

In place of the MR diagnostic apparatus provided in the specified exemplary embodiment for producing the images forming the basis for the treatment, other imaging systems can also be used, e.g. computed tomography systems, but also, in some circumstances, stereo X-ray installations or conventional X-ray installations.

In the above, when reference is made to the focus zone of the ultrasound serving for treatment, the spatial region surrounding the point of maximum sound pressure is to be understood, in that the intensity of the ultrasound is sufficient to achieve the desired therapeutic effect. Standardly, the focus zone is the region within the −6 db isobar, thus the region in which the sound pressure is at least equal to half the maximum sound pressure.

Although modifications and changes may be suggested by those skilled in the art, it is the intention of the inventors to embody within the patent warranted hereon all changes and modifications as reasonably and properly come within the scope of their contribution to the art.

We claim as our invention:

1. A therapy apparatus for treatment with acoustic waves, comprising:
   a source of acoustic waves and means for focusing said acoustic waves on a therapeutic effective region;
   displacement means for displacing the therapeutic effective region and a subject relative to one another;
   means for producing, at an arbitrary time and place, a first dataset identifying a spatial position of the therapeutic effective region and an orientation of the source relative to a first spatial coordinate system;
   means for producing, at an arbitrary time and place, a second dataset identifying a spatial position and an orientation of the subject relative to a second spatial coordinate system;
   display means for displaying, at an arbitrary time and place, an image of a portion of said subject, said portion containing a body region to be treated with the focused acoustic waves, and means for obtaining, on the basis of said image, a third dataset identifying a spatial position and orientation of said body region relative to a third spatial coordinate system;
   means for storing spatial position data identifying respective spatial positions of said first, second and third coordinate systems relative to each other; and
   means, supplied with said first, second and third datasets and with said spatial position data, for mixing a mark into said image, dependent on said first, second and third datasets and said spatial position data, indicating the position of said therapeutic effective region.

2. A therapy apparatus as claimed in claim 1 wherein said displacement means comprise a handheld, freely displaceable housing for said source.

3. A therapy apparatus as claimed in claim 1 wherein said displacement means comprise motorized adjustment means for positioning said source.

4. A therapy apparatus as claimed in claim 3 wherein said motorized adjustment means comprises a plurality of manually actuatable operating elements for selectively positioning said source.

5. A therapy apparatus as claimed in claim 1 further comprising:
   means for marking said body region with a marking identifying said body region,
   said marking being mixed into said image.

6. A therapy apparatus as claimed in claim 5 further comprising means for enabling said source for producing said acoustic waves only when said therapeutic effective region in said image is disposed within said body region identified in said image by said marking.

7. A therapy apparatus as claimed in claim 1 wherein said display means comprises means for displaying a tomogram of said subject.

8. A therapy apparatus as claimed in claim 1 wherein said display means comprises means for displaying a perspective image.

9. A therapy apparatus as claimed in claim 8 wherein said display means comprises means for displaying a perspective image partly in section.

10. A therapy apparatus as claimed in claim 1 wherein said display means comprises means for displaying a plurality of images simultaneously.

11. A therapy apparatus as claimed in claim 10 wherein said mixing means comprise means for mixing said mark indicating the position of said therapeutic effective region into more than one image in said plurality of images.

12. A therapy apparatus as claimed in claim 10 further comprising means for marking said body region with a marking identifying said body region, and wherein said mixing means comprises means for mixing said marking into more than one image in said plurality of images.

13. A therapy apparatus as claimed in claim 12 wherein said mixing means comprises means for mixing said mark indicating the position of the therapeutic effective region into more than one of said images in said plurality of images.

14. A therapy apparatus as claimed in claim 1 wherein said means for producing said first dataset include a three-dimensional navigation system.

15. A therapy apparatus as claimed in claim 1 wherein said means for producing said second dataset include a three-dimensional navigation system.

16. A therapy apparatus as claimed in claim 1 wherein said means for producing said first dataset includes a first three-dimensional navigation system and wherein said means for producing said second dataset includes a second three-dimensional navigation system.

17. A therapy apparatus as claimed in claim 1 wherein said display means include a surgical work station.

18. A therapy apparatus as claimed in claim 1 wherein said first and second coordinate systems are identical.

19. A therapy apparatus as claimed in claim 1 wherein said source comprises means for emitting focused ultrasound waves as said acoustic waves.

20. A therapy apparatus as claimed in claim 19 wherein said source comprises means for emitting said focused ultrasound waves with a first energy content for therapy and with a second energy content significantly less than said first energy content; and said therapy apparatus further comprising:

means for activating said source to emit said focused ultrasound waves with said second energy content for slightly elevating a temperature of tissue in said subject affected by said focused ultrasound waves with said second energy content; and image-producing means for producing an image of said subject wherein temperature differences are visible in said image, after activation of said source for emitting said focused ultrasound waves with said second energy content, and for operating said displacement means for adjusting said therapeutic effective region relative to said subject if a region of elevated temperature in said image produced by said image-producing means does not coincide with said therapeutic effective region.

21. A therapy apparatus as claimed in claim 20 wherein said image-producing means comprises means for producing a first image with no activation of said source, and for producing a second image after activation of said source for emitting said focused ultrasound waves with said second energy content, and wherein said image-producing means comprises means for producing said image wherein temperature differences are visible by comparison of said first and second images.

22. A therapy apparatus as claimed in claim 21 wherein said image-producing means comprises means for producing said image wherein said temperature differences are visible by subtraction of said first and second images.

23. A therapy apparatus as claimed in claim 20 wherein said image-producing means comprises an ultrasound diagnostic apparatus.

24. A therapy apparatus as claimed in claim 20 wherein said image-producing means comprises an MR diagnostic apparatus operated with temperature-sensitive measurement sequences.

25. A therapy apparatus as claimed in claim 1 wherein said display means comprises means for producing a first image during treatment and a second image after completion of at least a portion of treatment, and including means for comparing said first and second images for determining an extent of tissue modification in said subject caused by said acoustic waves.

26. A therapy apparatus as claimed in claim 25 wherein said means for comparing comprises means for subtracting said first and second images.

27. A therapy apparatus as claimed in claim 1 wherein said source of acoustic waves is physically separate from said means for producing a second data set.

28. A therapy apparatus for treatment with acoustic waves, comprising:

a source of acoustic waves and means for focusing said acoustic waves on a therapeutic effective region;

means for displacing said therapeutic effective region and a subject relative to one another;

means for producing, at an arbitrary time and place, a first dataset identifying a spatial position of the therapeutic effective region and an orientation of said source relative to a first spatial coordinate system;

means for producing, at an arbitrary time and place, a second dataset identifying a spatial position and an orientation of said subject relative to a second spatial coordinate system;

display means for displaying, at an arbitrary time and place, an image of a portion of said subject, said portion containing a body region to be treated with said focused acoustic waves and means for obtaining, on the basis of said image, a third dataset identifying a spatial position and orientation of said region to be treated relative to a third spatial coordinate system;

means for marking a body region to be treated on said subject and for mixing a marking identifying said body region into said image;

means for storing spatial position data identifying respective positions of said first, second and third coordinate systems relative to each other; and control means, supplied with said first, second and third datasets, with said spatial position data, and with data identifying a position of said marking in said image, for controlling operation of said displacement means, dependent on said first, second and third datasets, said spatial position data and said data identifying the position of said marking in said image, for causing said therapeutic effective region to lie in said body region to be treated and for identifying said therapeutic effective region with said marking.

29. A therapy apparatus as claimed in claim 28 further comprising means, supplied with said first, second and third datasets, said spatial position data and said data identifying the position of said marking in said image, for mixing a further mark into said image indicating a position of said therapeutic effective region in said image, dependent on said first, second and third datasets, said spatial position data, and said data identifying the position of said marking.

30. A therapy apparatus as claimed in claim 28 wherein said displacement means comprises motorized adjustment means, controlled by said control means, for positioning said source.

31. A therapy apparatus as claimed in claim 28 further comprising means for enabling said source for producing said acoustic waves only when said therapeutic effective region in said image is disposed within said body region identified in said image by said marking.

32. A therapy apparatus as claimed in claim 28 wherein said display means comprises means for displaying a tomogram of said subject.

33. A therapy apparatus as claimed in claim 28 wherein said display means comprises means for displaying a perspective image.

34. A therapy apparatus as claimed in claim 33 wherein said display means comprises means for displaying a perspective image partly in section.

35. A therapy apparatus as claimed in claim 28 wherein said display means comprises means for displaying a plurality of images simultaneously.

36. A therapy apparatus as claimed in claim 35 further comprising mixing means for mixing a mark indicating the position of said therapeutic effective region into more than one image in said plurality of images.

37. A therapy apparatus as claimed in claim 35 wherein said means for marking said body region with a marking identifying said body region, comprises means for mixing said marking into more than one image in said plurality of images.

38. A therapy apparatus as claimed in claim 37 further comprising mixing means for mixing a mark indicating the position of the therapeutic effective region into more than one of said images in said plurality of images.

39. A therapy apparatus as claimed in claim 28 wherein said means for producing said first dataset include a three-dimensional navigation system.

40. A therapy apparatus as claimed in claim 28 wherein said means for producing said second dataset include a three-dimensional navigation system.

41. A therapy apparatus as claimed in claim 28 wherein said means for producing said first dataset includes a first three-dimensional navigation system and wherein said means for producing said second dataset includes a second three-dimensional navigation system.

42. A therapy apparatus as claimed in claim 28 wherein said display means include a surgical work station.

43. A therapy apparatus as claimed in claim 28 wherein said first and second coordinate systems are identical.

44. A therapy apparatus as claimed in claim 28 wherein said source comprises means for emitting focused ultrasound waves as said acoustic waves.

45. A therapy apparatus as claimed in claim 44 wherein said source comprises means for emitting said focused ultrasound waves with a first energy content for therapy and with a second energy content significantly less than said first energy content; and said therapy apparatus further comprising:

means for activating said source to emit said focused ultrasound waves with said second energy content for slightly elevating a temperature of tissue in said subject affected by said focused ultrasound waves with said second energy content; and image-producing means for producing an image of said subject wherein temperature differences are visible in said image, after activation of said source for emitting said focused ultrasound waves with said second energy content, and for operating said displacement means for adjusting said therapeutic effective region relative to said subject if a region of elevated temperature in said image produced by said image-producing means does not coincide with said therapeutic effective region.

46. A therapy apparatus as claimed in claim 45 wherein said image-producing means comprises means for producing a first image with no activation of said source, and for producing a second image after activation of said source for emitting said focused ultrasound waves with said second energy content, and wherein said image-producing means comprises means for producing said image wherein temperature differences are visible by comparison of said first and second images.

47. A therapy apparatus as claimed in claim 46 wherein said image-producing means comprises means for producing said image wherein said temperature differences are visible by subtraction of said first and second images.

48. A therapy apparatus as claimed in claim 45 wherein said image-producing means comprises an ultrasound diagnostic apparatus.

49. A therapy apparatus as claimed in claim 45 wherein said image-producing means comprises an MR diagnostic apparatus operated with temperature-sensitive measurement sequences.

50. A therapy apparatus as claimed in claim 45 wherein said display means comprises means for producing a first image during treatment and a second image after completion of at least a portion of treatment, and including means for comparing said first and second images for determining an extent of tissue modification in said subject caused by said acoustic waves.

51. A therapy apparatus as claimed in claim 50 wherein said means for comparing comprises means for subtracting said first and second images.

52. A therapy apparatus as claimed in claim 28 wherein said source of acoustic waves is physically separate from said means for producing a second data set.

\* \* \* \* \*